(12) United States Patent
Desmet et al.

(10) Patent No.: US 11,900,252 B2
(45) Date of Patent: Feb. 13, 2024

(54) SYSTEM AND METHOD FOR EVALUATING THE PERFORMANCE OF A USER IN CAPTURING AN ULTRASOUND IMAGE OF AN ANATOMICAL REGION

(71) Applicant: CAE HEALTHCARE CANADA INC., Saint-Laurent (CA)

(72) Inventors: Laurent Desmet, Saint-Laurent (CA); Yannick Perron, Saint-Laurent (CA)

(73) Assignee: CAE HEALTHCARE CANADA INC., Saint-Laurent (CA)

( * ) Notice: Subject to any disclaimer, the term of this patent is extended or adjusted under 35 U.S.C. 154(b) by 0 days.

(21) Appl. No.: 17/970,396

(22) Filed: Oct. 20, 2022

(65) Prior Publication Data
US 2023/0037923 A1 Feb. 9, 2023

Related U.S. Application Data

(63) Continuation of application No. PCT/CA2022/050260, filed on Feb. 24, 2022.

(30) Foreign Application Priority Data

Feb. 26, 2021 (CA) .................. CA 3110581

(51) Int. Cl.
*G06N 3/08* (2023.01)
*G06N 3/045* (2023.01)
(Continued)

(52) U.S. Cl.
CPC ............... *G06N 3/08* (2013.01); *G06N 3/045* (2023.01); *G06V 10/82* (2022.01); *G06T 2207/20084* (2013.01)

(58) Field of Classification Search
CPC .......... G06N 3/08; G06N 3/045; G06V 10/82; G06T 2207/20084
See application file for complete search history.

(56) References Cited

U.S. PATENT DOCUMENTS 7,409,243 B2 * 8/2008 Nachaliel ............. A61B 5/0536
600/547
2008/0293029 A1 * 11/2008 Wilkins ............... G09B 23/286
434/272
(Continued)

FOREIGN PATENT DOCUMENTS

WO 2012123942 A1 9/2012
WO 2019243400 A1 12/2019
WO 2020162989 A1 8/2020

OTHER PUBLICATIONS

Meng-Chun Kao, Yu-Te Wu, Mei-Yung Tsou, Wen-Chuan Kuo, and Chien-Kun Ting Intelligent epidural needle placement using fiber-probe optical coherence tomography in a piglet model Taiwan Ministry of Science and technology Grant; National Health Research Institutes Pusblished by Biomedical Optics Express 3711, Aug. 1, 2018, vol. 9, N°8.
(Continued)

*Primary Examiner* — John W Lee
(74) *Attorney, Agent, or Firm* — KDW Firm PLLC (57) ABSTRACT

A training platform, a method and a computer-readable medium for evaluating users in capturing images of an internal anatomical region for the analysis of organs. Automated machine learning models, trained on a dataset of labelled training images associated with different imaging device positions, are used. The one or more automated machine learning models are used to process an image resulting from a user positioning an imaging device at various imaging device positions relative to a training manikin, a human or an animal, to determine whether the generated image corresponds to a predefined view required for the analysis of the organ features shown therein. An output indicative of whether the generated image corresponds to the predefined view expected for organ analysis and measurements is provided.

22 Claims, 5 Drawing Sheets

(51) Int. Cl.
*G06V 10/82* (2022.01)
*A61B 8/00* (2006.01)
*A61B 8/08* (2006.01)
*G09B 23/28* (2006.01)
*G09B 23/30* (2006.01)

(56) References Cited

U.S. PATENT DOCUMENTS

| | | | | |
|---|---|---|---|---|
| 2009/0287668 | A1* | 11/2009 | Evans | G06F 16/355 |
| | | | | 707/E17.046 |
| 2018/0042683 | A1* | 2/2018 | Cohen | G01S 5/16 |
| 2018/0336803 | A1 | 11/2018 | Patil et al. | |
| 2021/0110582 | A1* | 4/2021 | Sornes | G06N 3/045 |

OTHER PUBLICATIONS

First Exam Report for Canadian Application No. 3,110,581, dated Apr. 28, 2021, 5 pages.
Second Exam Report for Canadian Application No. 3,110,581, dated Sep. 1, 2021, 6 pages.
International Search Report and Written Opinion for the International Patent Application No. PCT/CA2022,050260, dated May 4, 2022, 11 pages.

* cited by examiner

SYSTEM AND METHOD FOR EVALUATING THE PERFORMANCE OF A USER IN CAPTURING AN ULTRASOUND IMAGE OF AN ANATOMICAL REGION

CROSS REFERENCE TO RELATED SPECIFICATION

This application is a continuation of Intl. Appln. No. PCT/CA2022/050260, filed Feb. 24, 2022, and which claims priority to Canadian Appln. No. 3,110,581, filed Feb. 26, 2021, each of which applications are incorporated by reference herein in their entirety for all purposes.

TECHNICAL FIELD OF THE INVENTION

The present invention relates to the field of healthcare training systems and methods, and more specifically relates to systems and methods for training users in capturing images of an anatomical region for organ analysis.

BACKGROUND

Healthcare training platforms help technicians and physicians learn how to use medical imaging systems, such as ultrasound systems, to generate images suitable for diagnosis and/or organ measurements.

There exist platforms that can be used for training on humans or animals, or on instrumented manikins. When used with manikins, ultrasound scans can be simulated based on the probe position relative to the manikin, where the ultrasound images are rendered from different 3D models that can include various pathologies. The training platforms help increase psychomotor and cognitive skills of trainees for probe handling and help in accelerating the learning process. They can be adapted to different applications, such as cardiac, pulmonary, abdominal, obstetrics and gynecological applications. The training platforms can guide trainees in acquiring the proper images for common target cut planes of organs.

Some of the existing training platforms include a software training application which can provide feedback to the trainee as to whether he or she acquired a proper scan image depending on whether the position of the probe is close or within a preregistered zone. There are, however, cases where artefacts, such as bones or fluids, prevent proper viewing of the organ(s), even if the probe is correctly positioned.

There is therefore a need for a system and a method that would provide improved feedback when assessing whether an image captured is suitable for anatomical analysis.

BRIEF SUMMARY OF THE INVENTION

According to an aspect, there is provided a computer implemented method for evaluating a performance of a user in capturing an image of an anatomical region, where the image is for organ analysis. The method comprises assigning a probe score based on a position of an imaging probe being manipulated by the user, compared to a previously determined valid probe position for a given view of the anatomical region. The method also comprises assigning an image score by processing the image associated with the position of the imaging probe using an automated machine learning model trained on a dataset of labelled training images associated with different imaging probe positions. The training images can comprise both valid and invalid images. The image score provided by the trained machine learning model can be indicative of a likelihood that the image is valid on the basis of similarities with the valid images. The method also comprises providing for output the probe score and the image score together providing an indication of whether the user has correctly positioned the imaging probe and of whether the image generated associated with the position and which has been at the probe position is usable for organ analysis.

In possible embodiments, the method further comprises determining the position of the imaging probe; and generating the image based on the position of the imaging probe.

In possible embodiments, the automated machine learning model is a neural network model.

In possible embodiments, the imaging probe is an ultrasound probe, and the image is an ultrasound image representing a cross sectional view of (an) organ(s) within the anatomical region.

In possible embodiments, the imaging probe is a simulated probe.

In possible embodiments, the position of the imaging probe is determined while a training manikin is within a field of view thereof. The method comprises rendering the simulated anatomical image associated with the determined position of the imaging probe, where the simulated anatomical image is extracted from a virtual 3D model of a human or animal.

In possible embodiments, the position of the imaging probe is determined while a human or an animal is within a field of view thereof, and wherein generating the image comprises capturing anatomical images in real time via the imaging probe.

In possible embodiments, the position of the imaging probe is determined by using one or more tracking devices that process position signals emitted by or received at the imaging probe.

In possible embodiments, the method comprises capturing a plurality of training images of at least one predetermined view of the anatomical region and classifying the training images as valid or invalid by assigning a binary label thereto, to generate the dataset of labelled training images.

In possible embodiments, the method comprises normalizing and or standardizing the training images and training the automated machine learning model using the dataset of labelled training images which have been normalized and or standardized.

In possible embodiments, the training images classified as invalid comprise artefacts preventing measurement and/or assessment of the organ(s), or portions thereof, in the anatomical region.

In possible embodiments, the artefacts comprise one or more of: bones, fluid, shadows, reverberations and/or lack of proper contrast of edges, cavities or sidewalls of the organs or the portions thereof.

In possible embodiments, the method comprises processing the training images by applying data augmentation algorithms thereto, to generate additional training images to increase a size of the dataset, the data augmentation algorithms comprising one or more of: a greyscale conversion algorithm, a rotation algorithm, a translation algorithm, a noise injection algorithm, and an edge detection algorithm.

In possible embodiments, the automated machine learning model is a convolutional neural network model having at least three layers of nodes, wherein a node has at least one weighted input, a transfer function to process the input, and an output.

In possible embodiments, the method comprises applying a focal loss function when training the convolutional neural network model.

In possible embodiments, the automated machine learning model is trained with training images classified and labelled for different views of the organs to be analyzed.

In possible embodiments, the image score is assigned using the automated machine learning model which is specifically trained for a given view of the anatomical region, the method further comprising using additional trained automated machine learning models for assessing captured images associated with additional views of the anatomical region.

In possible embodiments, the method comprises further providing for display a pass score or a fail score in real time, wherein the pass score corresponds to the probe score having reached or exceeded a probe score threshold and to the image score having reached or exceeded an image score threshold.

In possible embodiment, the pass score corresponds to the imaging probe being correctly positioned and the image being usable for anatomical analysis, and wherein the fail score corresponds to one of: the imaging probe being incorrectly positioned and the image being usable for anatomical analysis; the image probe being correctly positioned and the image being unusable for anatomical analysis; and the image probe being incorrectly positioned and the image being unusable for anatomical analysis.

In possible embodiments, the method comprises prompting the trainee to reposition the imaging probe until a performance score assigned thereto corresponds to the pass score.

According to another aspect, a computer implemented method for assessing whether an image of an internal anatomical region is usable for organ analysis is provided. The method comprises generating the image of the anatomical region based on an imaging probe position. The method also comprises processing the generated image using one or more automated machine learning models trained on datasets of training images, the training images comprising both valid and invalid images, the automated machine learning model(s) determining whether the image is usable for organ analysis by outputting an image score indicative of a likelihood that the image is valid on the basis of similarities with the valid images. The method also comprises providing for output a visual or audible indication of whether the generated image is usable for organ analysis based on said determination.

In possible embodiments, each of the one or more automated machine learning model is specifically trained for a given view of the anatomical region.

In possible embodiments, the method comprises capturing position signals associated with an imaging probe manipulated by a user; and calculating an imaging probe position based on the position signals captured.

In possible embodiments, the method comprises comparing the imaging probe position with a predetermined valid probe position, whether the imaging probe is correctly positioned for generating the given view of the anatomical region, wherein the visual or audible indication is also indicative of whether the imaging probe is correctly positioned.

In possible embodiments, at least some of the invalid images are associated with probe positions considered valid while comprising artefacts preventing proper measurements or assessment of organs.

In possible embodiments, at least some of the invalid images are associated with probe positions considered valid while comprising artefacts preventing proper measurements or assessment of organs.

According to another aspect, a computer implemented method is provided, for configuring a training system used for evaluating a performance of a user in capturing an image of an anatomical region that is usable for organ analysis. The method comprises generating a plurality of training images associated with an imaging probe being positioned at different positions relative to a training manikin, a human or an animal; classifying the training images as valid or invalid images by assigning a label thereto, wherein a valid image corresponds to a training image comprising a desired view of an organ, and an invalid image comprises a view where organs are either hidden, incorrectly oriented or unexploitable for anatomical analysis; and training one or more automated machine learning models using the training images labelled as valid or invalid to predict whether future captured images are interpretable for anatomical analysis when a probe is at or near one of the stored probe positions, a prediction outputted by the one or more machine learning model corresponding to a likelihood that the image is valid on the basis of similarities with the valid images.

According to an aspect, a training platform for training users in capturing images of an internal anatomical region for the analysis of organs is provided. The training platform comprises a processing device, in turn comprising a memory having stored thereon one or more automated machine learning models trained on a dataset of labelled training images associated with different imaging device positions, wherein the training images have been classified as valid or invalid for organ analysis The processing device also comprises a processor configured for processing, using the one or more automated machine learning models, a generated image resulting from a user moving an imaging device at various imaging device positions relative to a training manikin, a human or an animal, to determine whether the generated image corresponds to a predefined view required for the analysis of the organ features shown therein. The processor is also configured for providing an output indicative of whether the generated image corresponds to the predefined view expected for organ analysis and measurements, on the basis of similarities with the valid training images for the predefined view. The processor may also be configured to generate the image based on the position of an imaging device.

In possible embodiments, the training platform comprises the imaging device, and an image generating module for generating the images of the internal anatomical region; and a tracking system for determining the position of the imaging device.

In possible embodiments, the imaging device is a real or simulated ultrasound probe, and the image is a real or simulated ultrasound image representing a cross-sectional view of the organ(s) or portions thereof, within the anatomical region.

In possible embodiments, the one or more automated machine learning models comprises convolutional neural network models having at least three layers of nodes, wherein a node has at least one weighted input, a transfer function to process the input, and an output.

In possible embodiments, the training platform comprises one or more displays for displaying the generated image as the user moves the imaging probe, and for displaying a probe score and an image score, the probe score being indicative of a positional similarity between the position of the probe and (a) position(s) previously determined as valid, the image score being indicative of an image similarity between the generated image and valid image(s) previously determined as usable for organ analysis.

In possible embodiments, the training platform also comprises hardware components adapted to provide visual or audible indicators of a pass or fail score.

According to yet another aspect, a non-transitory computer-readable medium is provided. The non-transitory computer-readable medium has stored thereon processor-executable instructions for assessing whether an image of an internal anatomical region is usable for organ analysis, the instructions causing one or more processors to generate the image of the anatomical region based on an imaging probe position; process the generated image using one or more automated machine learning models trained on datasets of training images, the automated machine learning model(s) determining whether the image is usable for organ analysis; and provide for output a visual or audible indication of whether the generated image is usable for organ analysis based on said determination. The output can be derived from an image score provided by the trained machine learning model and being indicative of a likelihood that the image is valid on the basis of similarities with valid training images.

In possible embodiments, the non-transitory computer-readable medium further comprises instructions causing the one or more processors to calculate an imaging probe position based on position signals captured; and determine whether the imaging probe is correctly positioned by comparing the calculated imaging probe position with a predetermined valid probe position, wherein the output is also indicative of whether the imaging probe is correctly positioned.

In possible embodiments, the non-transitory computer-readable medium comprises instructions causing the one or more processors to generate a simulated anatomical image associated with the determined position of the imaging probe, the simulated anatomical image being extracted from a virtual 3D model of a human or animal.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which.

DETAILED DESCRIPTION

In the following description, the same numerical references refer to similar elements. The embodiments mentioned in the present description are embodiments only, given solely for exemplification purposes.

Moreover, although the embodiments of the method and system for evaluating the performance of a user in capturing images of anatomical regions consist of certain configurations as explained and illustrated herein, not all these configurations are essential and should not be taken in their restrictive sense. It is to be understood, as also apparent to a person skilled in the art, that other suitable components and cooperations therebetween, as well as other suitable configurations, may be used for the method and system for performing evaluations, as will be briefly explained herein and as can be easily inferred herefrom by a person skilled in the art.

Figure 1:
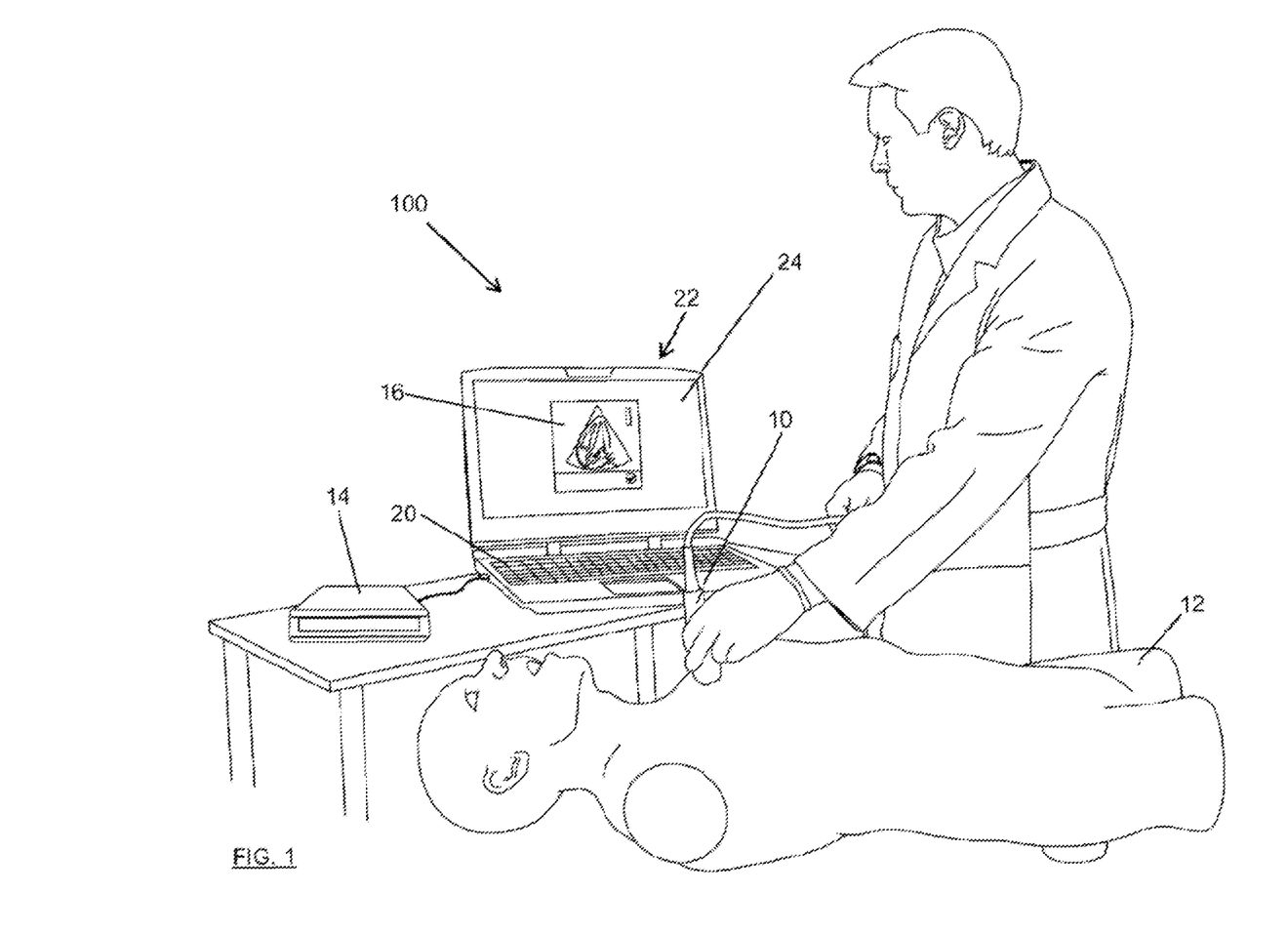
FIG. 1 is a schematic view of a user training on a training platform, according to a possible embodiment.

Referring to FIG. 1, a training platform or system 100 is schematically illustrated. The platform 100 can be used for training or for evaluating users in capturing images of an internal anatomical region for the analysis of organs. Users can be trainees, learning how to use a simulated or real imaging system, or medical staff, such as clinicians or veterinarians, that are using an imaging system in the normal course of their work on patients, and want feedback or guidance while manipulating an imaging probe 10. Images 16 are typically ultrasound images, but the platform can work for technologies other than ultrasound. The platform 100 is adapted and configurable to evaluate any type of images that can be captured or generated by an imaging probe which is moved or positioned relative to a body, an animal or a training manikin. For example, the image can be generated by a miniature camera moved into an artery or other part of a body or can be a florescence image generated by an imaging probe. The imaging probe 10 can be a real probe, such as an ultrasound probe, or a mock-up or simulated imaging probe, used for training purposes.

Still referring to FIG. 1, the platform 100 includes the imaging probe 10, a tracking system 14, for tracking the position of the imaging probe 10, and a processing device 20, which executes a dedicated software application 200 that processes information generated by the probe 10 and the tracking system 14, and generates images 16 for display on a graphical user interface 22. The platform 100 may include or not a training manikin 12. The imaging probe 10 may also be referred to as an image device or image transducer. The tracking system 14 can track the position and/or orientation of the probe, generally relative to a reference point, as is common in existing ultrasound training platforms. The tracking device 14 can be of different types. In FIG. 1, a Polhemus Patriot™ motion tracking device is used, which receives inputs from the imaging probe as it moves within an electromagnetic field generated by a source located in the training manikin 12, and relays the information in real time to the processing device 20, running the software evaluation application 200. It is also possible that the imaging probe 10 emits position signals, acting as a source, and that the receiver is located elsewhere. Other possible tracking systems include MEMS, gyros, accelerometers, magnetometers, and image-based tracking systems, as examples only. The connections between the imaging probe 10, the tracking system 14 and the processing device 20 can be wired or wireless. The position of the probe can be the X, Y and Z coordinates of a probe reference point, and/or angular positions $\Theta$, $\Phi$, $\Psi$ indicative of the pitch, yaw and roll of the imaging probe, relative to a reference frame. The tracking system 14 can thus provide at least 3DOF (Degree of Freedom) tracking of the probe, and preferably 6DOF. The origin of the reference frame can be on the training manikin or on the subject (human or animal) from which images are generated.

Figure 3:
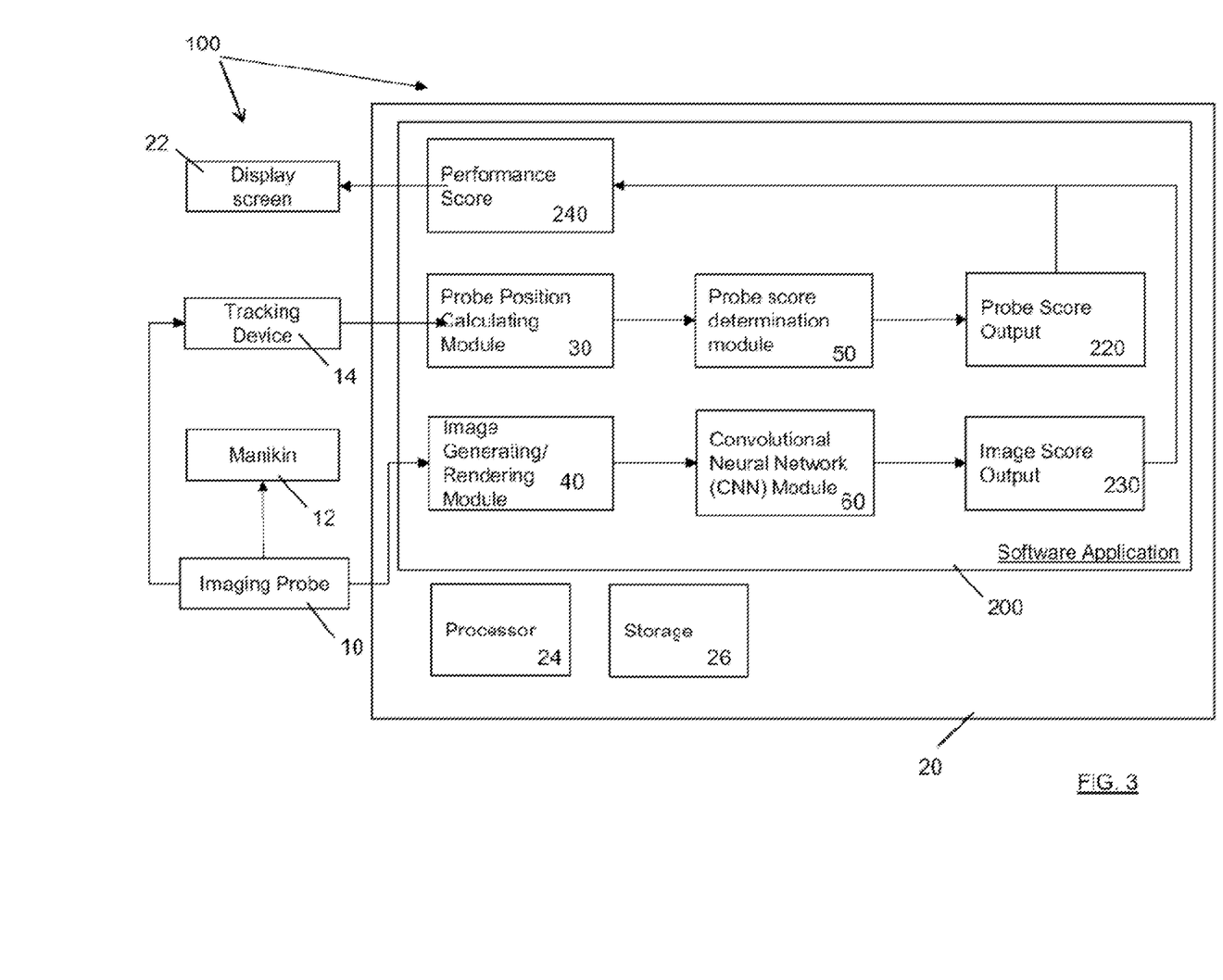
FIG. 3 is a schematic block diagram showing components of the training platform, according to a possible embodiment.

Referring to FIG. 1, and also to FIG. 3, the training platform 100 also comprises an image generating (or rendering) module 40, typically part of the software application 200 and running on device 20, for generating images of an internal anatomical region. While in the implementation illustrated, the image rendering module runs from the processing device 20, it is possible that the image generation is performed remotely, on cloud-based servers, for example. In fact, the different software modules of the software application 200 can run locally on device 20, or remotely, from one or more processing devices. The internal anatomical region can be part of a living human or animal, or the region can be part of a training manikin. Consequently, the image generating module 40 can generate real images, or simulated images. For example, the image generating module 40 can process the ultrasound signals sent and received by the probe, and generate real ultrasound images, in cases where the imaging probe is moved over, or relative to, a living or dead body. For training systems used in combination with manikins, the images can be simulated, by generating a given cut plane of a virtual 3D model of body or of a region of a body, as a function of the position of the imaging probe 10. In other words, the images 16 result from the user moving the imaging device 10 at various positions (referred to as imaging device positions) relative to a training manikin, a human or an animal. For ultrasound applications, the images represent cross-sectional views of the internal anatomical region. In other possible embodiments, the training platform 100 may solely include the processing device and associated software application, without the imaging probe, the probe position tracking device and/or the image generator. Outputs from the image probe, the tracking device and the image generator can be provided as inputs to the processing device and the software application, for assessing the usability of images captured by users while manipulating the imaging probe.

Still referring to FIGS. 1 and 3, the processing device 20 illustrated is a laptop provided with one or more processors, processor-readable medium storage (such as memory), communication ports and a display screen 22. However, in other embodiments, the processing device 20 can include one or more remote or local server(s), desktop computer(s), tablet(s) or any processing device(s) providing storage and processing capacities. The storage medium can include both volatile and non-volatile memory. The processing and memory storage can be distributed over several devices, or located in a single device, such as in FIG. 1, where the processing device is a portable computer. The processing device 20 runs the training or evaluating software application 200, which includes different software modules (distributed or not), and a graphical user interface to provide feedback to the user. The graphical user interface displays the images generated (real or simulated) and provide feedback to the user regarding its performance when manipulating the imaging probe 10, as is explained in greater detail below.

Figure 2:
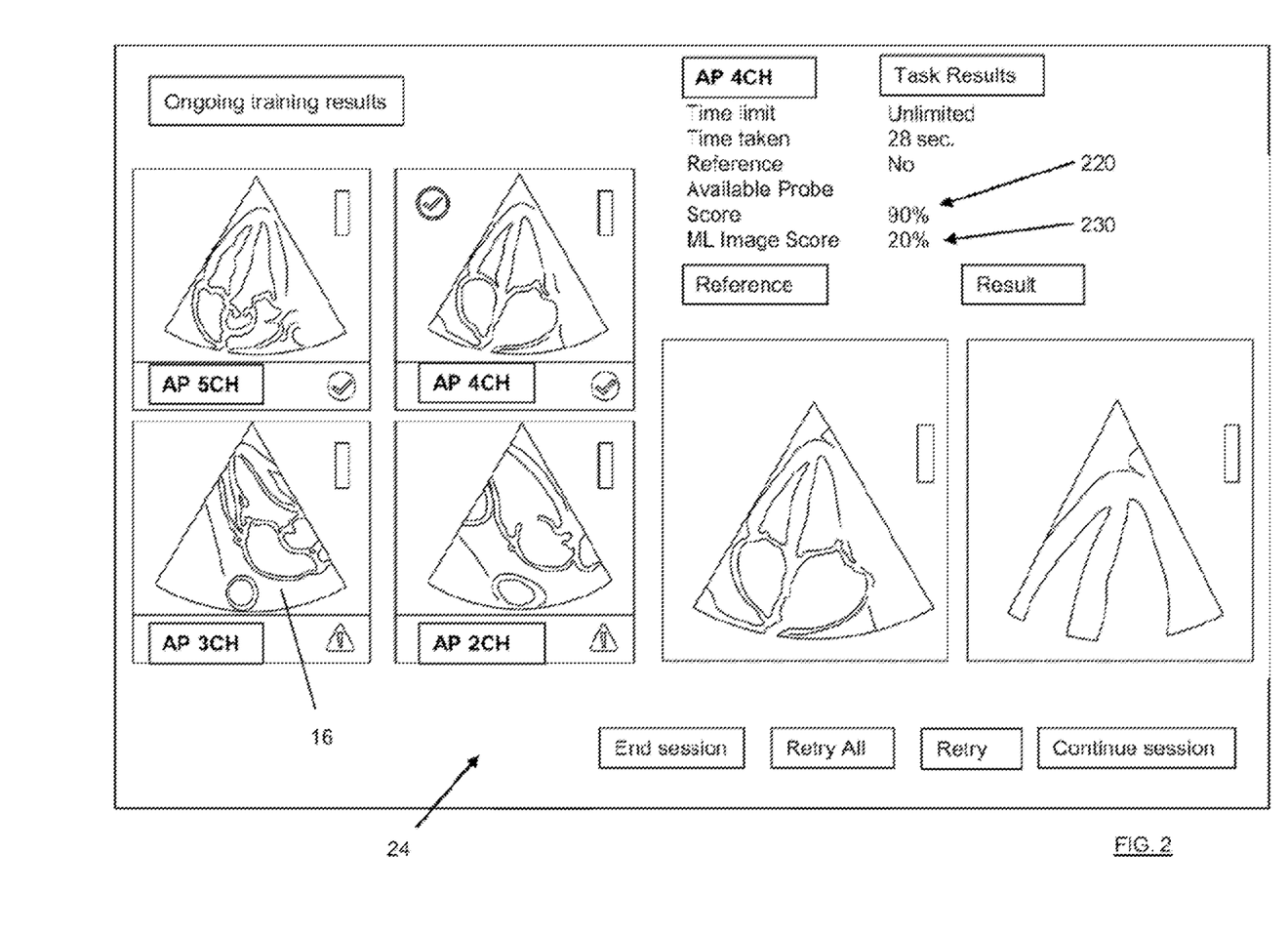
FIG. 2 shows a display screen with a graphical user interface displaying a probe score and an image score, according to a possible embodiment.

Still referring to FIGS. 1 and 3, and also to FIG. 2, in order to help trainees, the platform 100 provides an indication, via the graphical user interface 22, as to whether the imaging probe 10 is properly positioned and as to whether the image 16 generated at the probe position is usable for organ analysis and/or corresponds to a predefined view expected for organ analysis and measurement. The indication can be an output indicative of whether the generated image corresponds to the predefined view expected for organ analysis and measurements, on the basis of similarities with the valid training images for the predefined view. In the illustrated embodiment of the graphical user interface 24, the indication is provided as a probe score 220 and as an image score 230, respectively indicating how close the determined probe position and the image generated from this probe position are from an "ideal" or reference probe position, and from "ideal" or reference images, for a given target cut plane. The probe position calculating module 30 determines the position of the probe, based on information received from the tracking system 14. The probe score determination module 50 assigns a probe score 220 based on the position of the imaging probe compared to a previously determined valid probe position for a given view of the anatomical region.

In order to determine whether the image captured is usable (or exploitable) for organ analysis, one or more automated machine learning model(s) is/are used. More specifically, a neural network module 60, such as a convolutional neural network, is used to assign an image score 230 by processing the generated image 16 using the machine learning model trained on a dataset of labelled training images associated with different imaging probe positions. The training images may comprise both valid and invalid images. At least some of the invalid images may be associated with probe positions considered valid while comprising artefacts preventing proper measurements or assessment of organs. The image score provided by the trained machine learning model can be indicative of a likelihood or of a probability that the image is valid on the basis of similarities with valid training images. The image score provided by the trained machine learning model can also be indicative of a likelihood that the image pertains to a group of valid images. For example, a clustering machine learning model may assign the captured image with cluster of images previously determined as valid.

With regard to the determination of the probe score 220, an "ideal", "target" or "reference" preregistered position is stored in the storage memory of the processing device 20, and is associated to a given target cut plane or view, such as X, Y, Z coordinates and/or an orientation or attitude angles (pitch, row, yaw), relative to a reference frame or point. The tracking system 14 detect signals emitted or received by the imaging probe 10 or manikin 12 to determine the position of the probe 10. The position of the probe can also be determined by the probe position calculating module 30, part of the software application 200. Typically, for each medical application (such as cardiac, pulmonary, abdominal, etc.), standard views should be known and mastered by technicians and/or clinicians in order to assess the state of a given organ. For example, for cardiology ultrasound imaging, users should know how to perform a 2-chamber apical view, a 4-chamber apical view, right and left ventricular outflow views and 3-vessel views, as examples only. For each of a set of standard-plane cut views, a valid preregistered position is stored in the storage memory of the processing device 20. When a trainee moves the imaging probe 10 on or near the subject (human, animal or manikin), the probe score determination module 50 calculates a distance or deviation between the actual probe position and the registered/ideal probe position. The calculated probe distance can be normalized, and a probe score 220, such as a percentage from 0-100% can be provided for display on the display screen. The closer the actual probe position is to the preregistered position, the higher the score. Of course, other types of indicators are possible, such as pass or fail scores, color codes, vibrations or audible indicators. The position tracking system 14 is thus configured to provide information indicative of an orientation of the imaging probe 10, and the processing device 20 is configured to determine whether the imaging probe 10 is correctly positioned for generating one of the predetermined views by comparing the position and/or the orientation of the imaging probe to previously determined valid probe positions for said one predetermined view.

While the probe score generally provides proper feedback to users, it is possible that a high probe score is returned, while the view is not usable or exploitable for organ analysis. For example, when the probe is positioned between two ribs, the difference between the probe being correctly positioned (for example at P1) and incorrectly positioned (P2), such as if the probe even just slightly overlaps one rib, is so slight that the probe score will be about the same for both positions. However, in the first case, the image captured at P1 is valid and usable for organ analysis, while the image captured at P2 is invalid and unusable, since a portion of the rib blocks partially or entirely the organ to be measured or assessed. In other cases, the accuracy of the probe position can be affected by the presence of interfering objects, such as metal tables, electric motors, strong speakers, electric wires, etc. The probe score 220 alone can thus lead to false positives and is not entirely reliable to evaluate users' ability in capturing proper anatomical images.

Figure 4A:
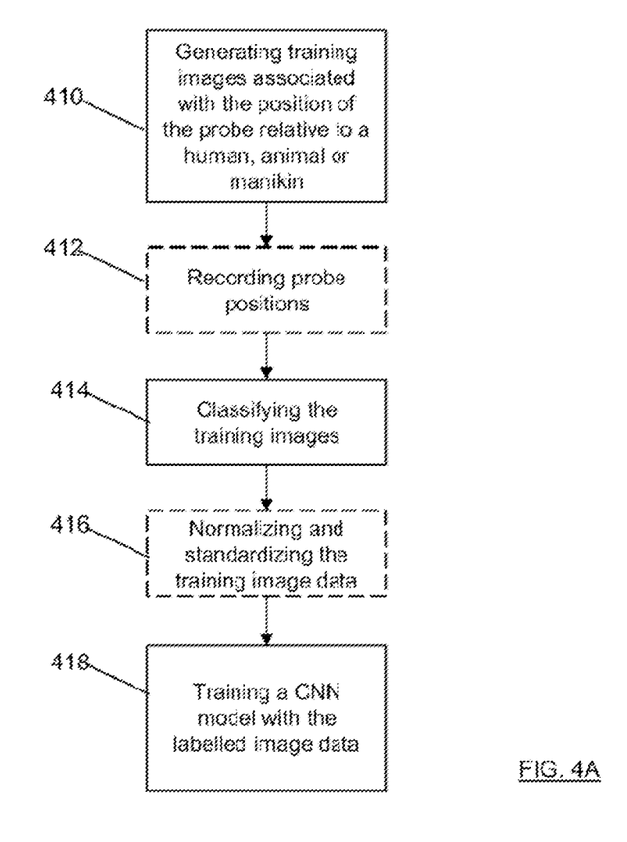
FIG. 4A is a flow chart showing steps for generating images and training a neural network model for assessing whether an image captured with the training platform is exploitable or not for organ analysis, according to a possible embodiment.
Figure 4B:
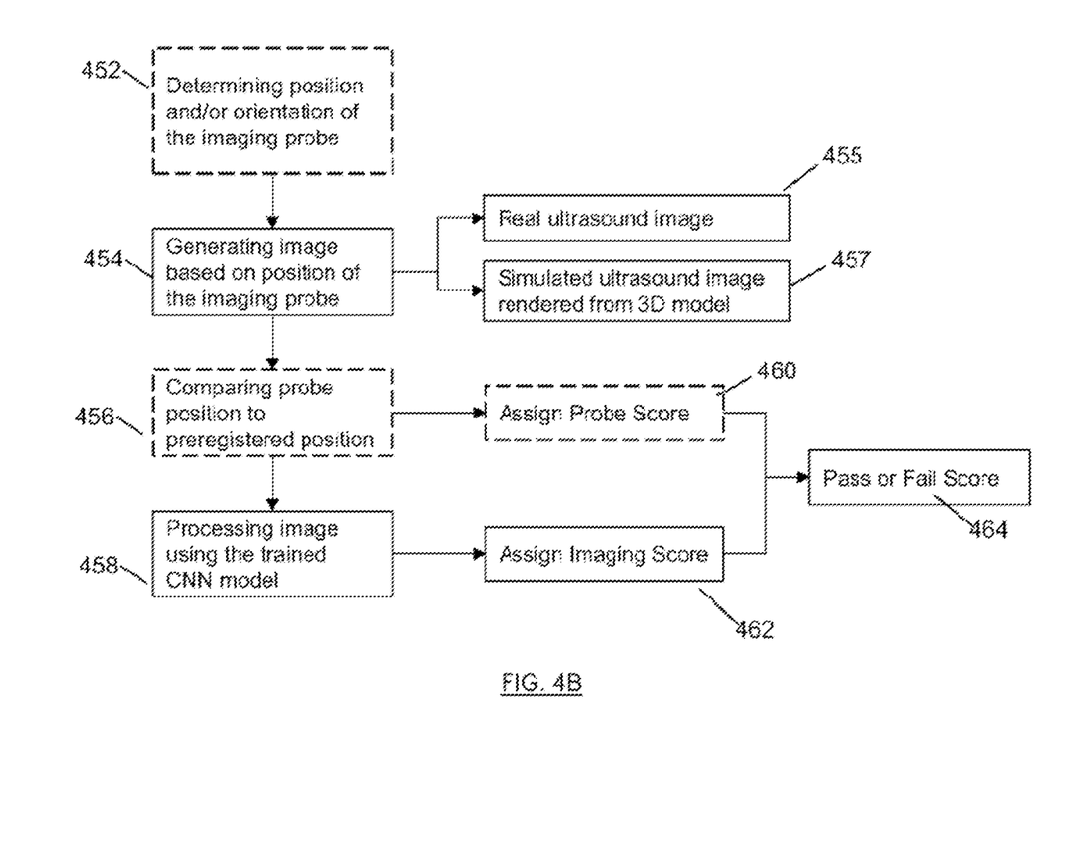
FIG. 4B is a flow chart showing steps for evaluating a performance of a user in capturing an image of an anatomical region, according to a possible embodiment.

Still referring to FIG. 3, and also to FIGS. 4A and 4B, the proposed method and platform comprise using an automated machine learning model trained on a dataset of training images, previously determined as valid or invalid by an expert. Machine learning model encompasses computer programs, algorithms and/or libraries that learn and can process data based on previously categorized or labelled data. In the context of the present description, the training images are of the same type as the images generated by the users being evaluated, and can be real ultrasound images (455), generated through the probe, when moved over a human or an animal, or simulated images (457), in cases where the probe is moved over or near a training manikin. In the latter case, the training images are rendered by using a virtual 3D model, according to the position of the probe, as explained earlier. The training process thus starts with the step 410 of generating training images, in FIG. 4A. Probe positions are also preferably recorded (step 412) and associated with each of the training images. The probe can be physically moved relative to a human or training manikin, within the field of view of the probe, but not necessarily. The probe can also be positioned using a probe positioning algorithm, for applications where the training or evaluating process is performed in a virtual environment. It will be noted that while step 412 is shown after step 410, this step can occur prior to or simultaneously to step 410. Alternatively, the training images can be associated with a given plane cut or view. In possible embodiments, the evaluation of whether an image captured by the imaging probe could be based solely on the image captured, without assessing in parallel proper positioning of the image probe. In such cases, there would be no need to record valid or invalid probe positions, and thus step 412 would be omitted.

In order to train the neural network model 60, a large dataset of images is preferably used, such as over thousands of images. Alternatively, it is possible to use a reduced set of training images, such as about a hundred images, and expand them into a larger dataset by applying data augmentation algorithms. Data augmentation algorithms can comprise greyscale conversion algorithms, rotation algorithms, translation algorithms, noise injection algorithms and edge detection algorithms. The data augmentation algorithms can modify the gain, contrast and/or gradient variations of the image pixels; and perform translation and/or rotational operations on the images. Thus, from a single training image, several additional training images can be generated by applying different transformations to the training images, via the data transformation algorithms. The expanded set of training images can then be used for classification, i.e., as valid/usable vs invalid/unusable for organ analysis. For images previously determined as usable, the data augmentation algorithms are preferably chosen and applied to make sure the images are still valid and usable after having been modified. As an example, recording a video sequence of the images generated by an expert moving the probe can be performed to create the set of training images, and from the video sequence, images can be extracted and classified, and expanded, a posteriori. The dataset of training images (whether originating from a large data set or from a reduced dataset expanded with data augmentation) include both valid and invalid images that are classified or labelled in order to be used for training the neural network, by assigning a binary label to each training image, as in step 416. As an example, training images classified as invalid can comprise artefacts, such as bones, fluid, shadows, reverberations and/or lack of proper contrast of edges, cavities or sidewalls of the organs or the portions thereof, where the artefacts prevent measurement and/or assessment of the organ(s), or portions thereof, in the anatomical region. The training of the neural network is thus a supervised training, since the images are previously classified/labelled. Regarding the classification process, the images can be further labelled according to specific views of the organs to be analyzed. For example, for cardiology applications, the training images can be further classified or labelled depending on whether they show 2, 3 or 4 chamber images.

Before processing the images through the neural network model for training, the image data may optionally be preprocessed. For example, preprocessing the images can include normalizing the images, for example such that at least some of the image attribute values, such as pixel values, range between 0 and 1. One possible option is to normalize a histogram of the pixel values. Another possible option for preprocessing the images includes standardizing them, for example by dividing all pixel values and color channels (such as Red, Green and Blue channels) by 255. The image raw data may comprise attributes with varying scales. Normalizing or standardizing the image raw data allows for all images to share a common scale, without distorting the variations of the different attributes. The normalizing or standardizing of the training image data (step 416) can be performed before or after other image-processing operations but prior to being fed to the automated machine learning models.

Once the training image data has been preprocessed (step 414) such as normalized or standardized, and labelled (step 416), an artificial neural network can be trained (step 418). The neural network model preferably a convolutional neural network (CNN) comprising at least three layers of nodes, wherein each node has at least one weighted input, a transfer function to process the input, and an output. At the beginning of the training process, the feature maps of the CNN model are randomly set. As training images are fed or processed through the CNN model, weights associated to each feature (also referred to as filters) are continuously adjusted, until all training images have been processed. A cross entropy loss function can be used to optimize the parameter values (weights) in the neural network model. The loss is calculated using a loss function to match the target value (in this case, valid or invalid image) and the predicted value by the neural network. A gradient descent is then used to update the weights to minimize loss. Preferably, a «focal loss» function is used. According to possible embodiments, more than one neural network can be trained, such that each of the several neural networks is specifically trained for a distinct type of view or target plane cut of the anatomical region. For example, the application 200 can comprise a first CNN model trained on images relating to a first target cut plane, such as a 2-chamber apical view for cardiology applications; a second CNN model trained on images relating to a second target cut plant, such as a 4-chamber apical view, and so on. Having CNN models specifically trained for specific views or target cut planes may help decrease the time for training the model and/or increase the accuracy of the image assessment, when evaluating a user. According to other implementations, in order to train a machine learning model to process images of organs other than the one on which is has been already trained, it is possible to train the same machine learning model by applying "transfer learning". In the case of a trained neural network model, the weights have already been properly initialized for a first organ. In order to train the same neural network model for other organs, less training images are required since the weights of the different nodes have been previously set for a first organ. The number of image and/or processing time is thereby reduced, and the neural network can be more rapidly configured for being able to correctly assess captured images of the new/additional organs.

Referring to FIGS. 3 and 4B, a flow chart of the general steps for evaluating the performance of a user in capturing an image of an anatomical region, using the platform 100, are illustrated. While the user manipulates or positions the imaging probe, the position of the probe is determined (step 452), and one or more images are generated based on the position of the imaging probe (step 454). The position of the imaging probe and the images are preferably continuously generated, but may also be periodically generated, or generated in response to a user input. A determination is made as to whether the imaging probe is correctly positioned for generating a specific view of the anatomical region, by comparing its position as calculated by a probe tracking system and/or probe score calculating module, against a predetermined valid probe position (step 456). Depending on this determination, a probe score 220 is assigned (step 460) and can be presented to the user via the graphical user interface. This probe score 220 can be a pass or fail score, or a number, comment or icon indicating how close the actual probe position is from the target probe position. Alternatively, an audible indication can inform the user as to whether the probe is properly positioned or not.

During a concomitant period, but not necessarily, the images generated by the image rendering module 40 are processed using the trained CNN model step 458), which outputs or assigns an image score 230 indicative how close or similar the captured image is from reference or target images, previously determined as valid. The captured/generated images are preprocessed, such as normalized or standardized, with the same preprocessing operations used on the training images, prior to being fed to the trained CNN model. Depending on the configuration of the CNN module 60, the image score 230 can be assigned (step 462) using a neural network model which is specifically trained for a given view of the anatomical region. Additional trained neural network models can be used for assessing captured images targeting additional views of the anatomical region. Feedback provided by the platform 100 to the user regarding the usability of the image captured for a given targeted view can also be any type of visual or audible indication.

While not essential, it is best to combine the probe score 220 with the image score 230, since otherwise the neural network model may be unable to distinguish two images that are mirrored or inverted. By combining the probe score 220 and the image score 230, the training platform provides better feedback to users, regarding both the orientation/position of the images and the content of the image. In possible embodiment, a pass or fail score 464 can be provided for display on the graphical user interface, preferably in real time, wherein a pass score corresponds to the probe score 220 having reached or exceeded a probe score threshold and to the image score 230 having reached or exceeded an image score threshold. A pass score can thus correspond to the imaging probe 10 being correctly positioned and the generated image being usable (or exploitable) for anatomical analysis, and wherein a fail score corresponds to one of: the imaging probe being incorrectly positioned and the generated image being usable for anatomical analysis; the image probe being correctly positioned and the generated image being unusable for anatomical analysis; and the image probe being incorrectly positioned and the generated image being unusable for anatomical analysis. In possible embodiments, the graphical user interface 24 may prompt the user or trainee to reposition the imaging probe until the performance score assigned thereto corresponds to the pass score.

As can be appreciated, the use of a trained neural network model to assess whether images generated at a given image probe position are usable for organ analysis or assessment allows improving feedback provided to users and increases reliability in assessing the performance of users or trainees. While the imaging probe may seem to be correctly positioned, the probe may still be capturing invalid images of the targeted anatomical region, since artefacts can block or affect proper view of organs. The proposed method and platform allow overcoming such drawbacks in diminishing false positives.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications can be made.

The invention claimed is:

1. A computer implemented method for evaluating a performance of a user in capturing an image of an anatomical region, the image being for organ analysis, the method comprising:

generating the image based on a position of an imaging probe;

assigning a probe score based on the position of the imaging probe being manipulated by the user compared to a previously determined valid probe position for a given view of the anatomical region;

assigning an image score by processing the image associated with the position of the imaging probe using an automated machine learning model trained on a dataset of labelled training images associated with different imaging probe positions, the training images comprising both valid and invalid images, the image score provided by the trained machine learning model being indicative of a likelihood that the image is valid on the basis of similarities with the valid images; and providing for output the probe score and the image score together providing an indication of whether the user has correctly positioned the imaging probe and of whether the image associated with the position and which has been generated at the probe position is usable for organ analysis.

2. The computer implemented method of claim 1, wherein the imaging probe is an ultrasound probe, and the image is an ultrasound image representing a cross sectional view of (an) organ(s) within the anatomical region.

3. The computer implemented method of claim 1, wherein the imaging probe is a simulated probe and wherein the position of the imaging probe is determined while a training manikin is within a field of view thereof, and wherein generating the image comprises rendering a simulated anatomical image associated with the determined position of the imaging probe, the simulated anatomical image being extracted from a virtual 3D model of a human or animal.

4. The computer implemented method of claim 1, wherein the position of the imaging probe is determined while a human or an animal is within a field of view thereof, and wherein generating the image comprises capturing anatomical images in real time via the imaging probe.

5. The computer implemented method of claim 1, wherein the position of the imaging probe is determined by using one or more tracking devices that process position signals emitted by or received at the imaging probe.

6. The computer implemented method of claim 1, further comprising:
capturing a plurality of training images of at least one predetermined view of the anatomical region and classifying the training images as valid or invalid by assigning a binary label thereto, to generate the dataset of labelled training images; and
normalizing or standardizing the training images and training the automated machine learning model using the dataset of labelled training images which have been normalized or standardized.

7. The computer implemented method of claim 6, comprising processing the training images by applying data augmentation algorithms thereto, to generate additional training images to increase a size of the dataset, the data augmentation algorithms comprising one or more of: a greyscale conversion algorithm, a rotation algorithm, a translation algorithm, a noise injection algorithm, and an edge detection algorithm.

8. The computer implemented method of claim 1, wherein the automated machine learning model is a convolutional neural network model having at least three layers of nodes, wherein a node has at least one weighted input, a transfer function to process the input, and an output.

9. The computer implemented method of claim 8 further comprising applying a focal loss function when training the convolutional neural network model.

10. The computer implemented method of claim 6, wherein the automated machine learning model is trained with training images classified and labelled for different views of the organs to be analyzed.

11. The computer implemented method of claim 1, wherein the image score is assigned using the automated machine learning model which is specifically trained for a given view of the anatomical region, the method further comprising using additional trained automated machine learning models for assessing captured images associated with additional views of the anatomical region.

12. The computer implemented method of claim 1, comprising prompting the trainee to reposition the imaging probe until a performance score assigned thereto corresponds to the pass score.

13. A computer implemented method for assessing whether an image of an internal anatomical region is usable for organ analysis, the method comprising:
generating the image of the anatomical region based on an imaging probe position;
processing the generated image using one or more automated machine learning models trained on datasets of labelled training images, the labelled training images being associated with an imaging probe positioned at different positions relative to a training manikin, a human or an animal, the labelled training images having been classified as valid or invalid images by assigning a label thereto, a valid image corresponding to a target cut plane of an organ, and at least some of the invalid images corresponding to a cut plane where the organ is at least partially hidden or incorrectly oriented, the automated machine learning model(s) determining whether the generated image is usable for organ analysis by outputting an image score indicative of a likelihood that the image is valid on the basis of similarities with the labelled training images classified as valid; and
providing for output a visual or audible indication of whether the generated image corresponds to the target cut plane based on said determination.

14. The computer implemented method of claim 13, wherein each of the one or more automated machine learning model is specifically trained for a given target cut plane of the anatomical region.

15. The computer implemented method of claim 13, further comprising:
capturing position signals associated with an imaging probe manipulated by a user; and
calculating an imaging probe position based on the position signals captured.

16. The computer implemented method of claim 15, further comprising determining, by comparing the imaging probe position with a predetermined valid probe position, whether the imaging probe is correctly positioned for generating the given target cut plane of the anatomical region, wherein the visual or audible indication is also indicative of whether the imaging probe is correctly positioned.

17. A training platform for training users in capturing images of an internal anatomical region for the analysis of organs, the training platform comprising:
a processing device comprising:
a memory having stored thereon one or more automated machine learning models trained on a dataset of labelled training images associated with different imaging device positions, wherein the labelled training images have been classified as valid or invalid for organ analysis by assigning a label thereto, a valid image corresponding to a target cut plane of an organ, and at least some of the invalid images corresponding to a cut plane where the organ is at least partially hidden or incorrectly oriented; and a processor configured for:

processing using the one or more automated machine learning models a generated image resulting from a user moving an imaging device at various imaging device positions relative to a training manikin, a human or an animal, to determine whether the generated image corresponds to a predefined target plane required for the analysis of the organ features shown therein, by outputting an image score indicative of a likelihood that the generated image is valid on the basis of similarities with the valid images; and providing an output indicative of whether the generated image corresponds to the target cut plane expected for organ analysis and measurements on the basis of similarities with the valid training images for the predefined view.

18. The training platform of claim 17, further comprising the imaging device; an image generating module for generating the images of the internal anatomical region; and a tracking system for determining the position of the imaging device.

19. The training platform of claim 17, wherein the imaging device is a real or simulated ultrasound probe, and the image is a real or simulated ultrasound image representing a cross-sectional view of the organ(s) or portions thereof, within the anatomical region.

20. The training platform of claim 17, further comprising one or more displays for displaying the generated image as the user moves the imaging probe, and for displaying a probe score and an image score, the probe score being indicative of a positional similarity between the position of the probe and (a) position(s) previously determined as valid.

21. The computer implemented method of claim 13, wherein the visual or audible indication is derived from the image score output by the one or more automated machine learning models.

22. The training platform of claim 17, wherein the output is a visual or audible indication is derived from the image score output by the one or more automated machine learning models.

* * * * *